United States Patent
Hazewinkel et al.

(10) Patent No.: US 7,507,391 B2
(45) Date of Patent: Mar. 24, 2009

(54) PROCESS AND APPARATUS FOR THE PRODUCTION OF SULPHUR OXIDES

(75) Inventors: Jacob Hendrik Obbo Hazewinkel, Zoetermeer (NL); Johannes Wouterus Van Groenestijn, Apeldoorn (NL); Koen Peter Henri Meesters, Amersfoort (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 11/837,141

(22) Filed: Aug. 10, 2007

(65) Prior Publication Data

US 2008/0038184 A1 Feb. 14, 2008

Related U.S. Application Data

(63) Continuation of application No. PCT/NL2006/000075, filed on Feb. 13, 2006.

(30) Foreign Application Priority Data

Feb. 11, 2005 (EP) .................................. 05075351

(51) Int. Cl.
*C01B 17/48* (2006.01)
*C01B 17/50* (2006.01)
*C01B 17/52* (2006.01)
*C01B 17/74* (2006.01)
*C13K 1/02* (2006.01)
*C12P 7/10* (2006.01)

(52) U.S. Cl. ................. 423/532; 423/539; 423/540; 423/542; 210/916; 127/37; 435/165

(58) Field of Classification Search ............... 423/532, 423/539, 540, 542; 210/916; 127/37; 435/165
See application file for complete search history.

(56) References Cited

U.S. PATENT DOCUMENTS

| 2,675,297 | A | * | 4/1954 | Gray et al. .................. 423/428 |
| 3,821,110 | A | * | 6/1974 | Luetzelschwab ............. 210/750 |
| 4,241,040 | A | | 12/1980 | Van Pool ..................... 423/542 |
| 4,288,286 | A | * | 9/1981 | Fuller ........................ 162/30.11 |
| 5,928,620 | A | | 7/1999 | Lynn ......................... 423/574.1 |

FOREIGN PATENT DOCUMENTS

| DE | 0 376 633 | 11/1922 |
| DE | 43 04 143 | 8/1994 |
| EP | 1 127 850 | 8/2001 |

OTHER PUBLICATIONS

English abstract of DE 43 04 143 (Aug. 18, 1994).*
von Sivers and Zacchi, "Ethanol from Lignocellulosics: A Review of the Economy," *Bioresource Technology*, 56:131-140, (1996).

* cited by examiner

*Primary Examiner*—Timothy C Vanoy
(74) *Attorney, Agent, or Firm*—Banner & Witcoff, Ltd.

(57) ABSTRACT

Sulphur oxides are generated from a liquid stream of hydrogen sulphide by feeding the liquid stream to a vacuum stripper where the stream is contacted with a stripping gas including steam under reduce pressure. Hydrogen sulphide is transferred to the stripping gas, whereby a loaded stripping gas is obtained. Water in the loaded stripping gas is condensed producing a H2S rich stream. The H2S is then burned in the stream to produce a stream rich in oxides of sulphur.

20 Claims, 1 Drawing Sheet

PROCESS AND APPARATUS FOR THE PRODUCTION OF SULPHUR OXIDES

RELATED APPLICATIONS

This application is a continuation of PCT application no. PCT/NL2006/000075, designating the United States and filed Feb. 13, 2006; which claims the benefit of the filing date of European application no. 05075351.6, filed Feb. 11, 2005; each of which is hereby incorporated herein by reference in its entirety for all purposes.

FIELD

The invention is directed to a process and apparatus for the removal of hydrogen sulphides from streams containing them, in particular from wastewater streams, and production of sulphur oxides from said removed hydrogen sulphides.

BACKGROUND

In many industrial production processes a stream containing organic material and sulphate is produced, in particular in production processes wherein organic material and sulphuric acid are used. Examples of such processes are processes which involve the use of sulphuric acid for the release and hydrolysis of lignocellulose, so that the sugar containing groups that are thus produced can be used in a fermentation process for the production of ethanol, lactic acid, citric acid, and the like. Commonly the sulphate in these streams is converted to hydrogen sulphide, in particular using anaerobic treatment processes, after which a step is carried out for removing the hydrogen sulphide.

In the art several processes are known for removing hydrogen sulphide from process gases. U.S. Pat. No. 5,928,620, for example, discloses a process wherein $H_2S$ is converted to elemental sulphur.

SUMMARY

The present invention seeks to provide an efficient process for removing $H_2S$ from process streams. At the same time, the process should make it possible that the removed $H_2S$ may be converted into useful sulphur oxide compounds.

It was found that this object can be met by removing $H_2S$ from process streams, in particular from liquid process streams, more particularly aqueous process streams, by vacuum stripping followed by burning of the removed $H_2S$. Thus in one embodiment, the present invention is directed to a process for the removal of hydrogen sulphide from a liquid stream, comprising the steps of
feeding said liquid stream to a stripper;
contacting said liquid stream in said stripper under reduced pressure with a stripping gas, which stripping gas comprises steam that is generated in said stripper, whereby at least part of said hydrogen sulphide is transferred to said stripping gas, whereby a loaded stripping gas is obtained;
subjecting said loaded stripping gas from said vacuum stripper to a step wherein water is condensed, thus producing a $H_2S$ rich stream; and
burning $H_2S$ in said $H_2S$ rich stream, preferably using air, thus producing a stream rich in oxides of sulphur.

BRIEF DESCRIPTION OF THE DRAWING

The foregoing and other features and advantages of the present invention will be more fully understood from the following description of an illustrative embodiment taken in conjunction with the following drawing in which.

DETAILED DESCRIPTION

Figure 1:
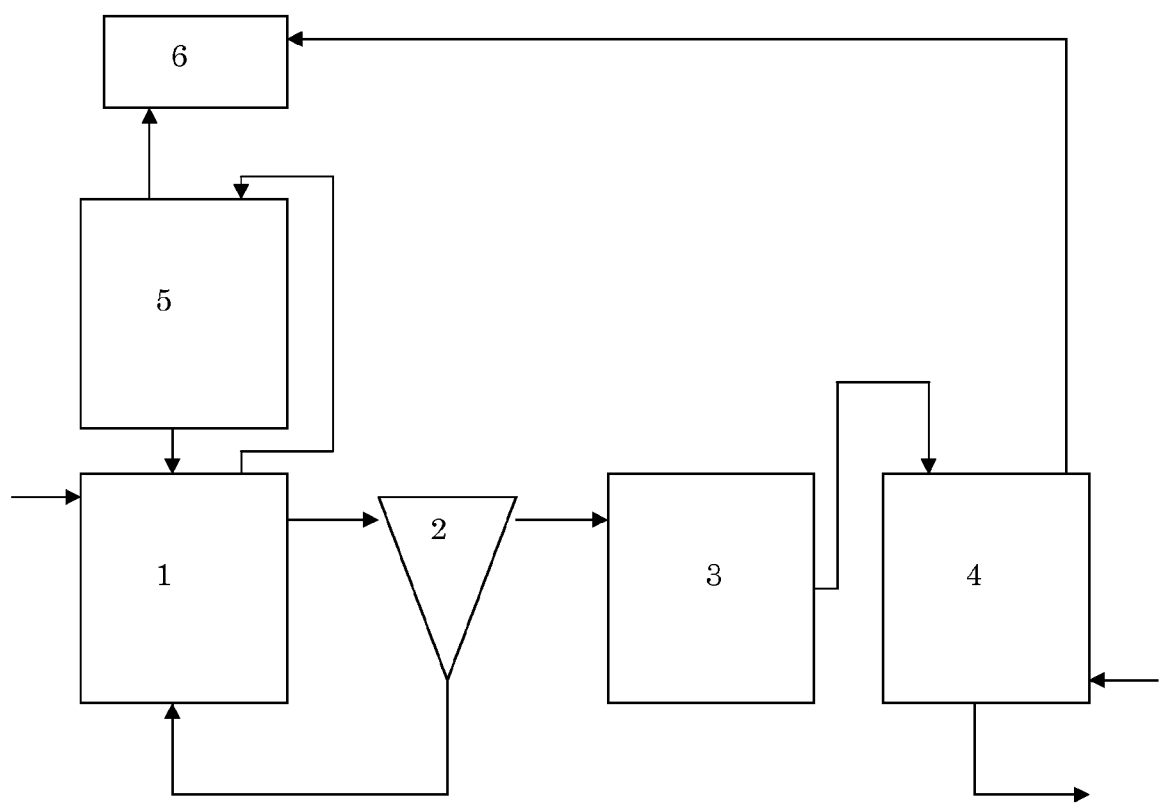
FIG. 1 schematically depicts an embodiment utilizing two strippers.

In accordance with the present invention an aqueous solution of sulphide may be used. Aqueous hydrogen sulphide containing solutions may originate e.g. from anaerobic bioreactors, in which sulphur compounds (e.g. sulphate, sulphite, thiosulphate, certain amino acids, etc.), are converted to sulphide, while organic compounds are used as an electron donor. Also $H_2$, electricity and redox mediators can be used as electron donor. The use of aqueous sulphide containing streams in accordance with the present invention is particularly advantageous, because the gas that is produced in the vacuum stripper, comprises water vapour and hydrogen sulphide. It was found that the steam in this gas stream can be condensed relatively easily, whereby a gas stream with a high hydrogen sulphide concentration is obtained.

One particular type of bioprocesses are anaerobic biological acidifying processes, in which the organic material is mainly converted into fatty acids, which fatty acids are in turn not converted to methane and $CO_2$. By result, the fatty acids accumulate and the pH drops. A low pH is favourable for subsequent sulphide removal, as can be explained by the following reaction equations:

$$S_2^- + H^+ \leftrightarrow HS^- \qquad (1)$$

$$HS^- + H^+ \leftrightarrow H_2S \qquad (2)$$

At increased $H^+$ concentrations, the equilibrium of (2) shifts to the right hand side and the $H_2S$ concentration increases. By result, the $H_2S$ can be transferred more easily to the stripping gas. Thus acidifying bioprocesses are preferred according to the present invention. For this type of processes it was found that the suitable pH is preferably from 6 to 6.9, in particular about 6.5.

The contacting of the stripping gas and the $H_2S$ containing liquid may be carried out in various ways. The stripping gas may be directed through the liquid in the form of bubbles. It is also possible to have the gaseous phase as the continuous phase and finely divide the liquid, e.g. by spraying the liquid from the top of the stripping column. In the latter case, it is usually preferred to have column packings present in the stripper, in order to increase the contact area between stripping gas and liquid. Preferred packings are Pall rings and/or saddle rings. Usually, when a strip gas is to be added to the stripper, the gas is fed at the bottom and the liquid at the top.

DE-A-376 633 describes a vacuum stripping method which involves heating under vacuum. Such a method is disadvantageous because it requires more energy. Furthermore, this method is not suitable for treating a liquid feed stream that originates from a bioreactor and comprises living bacteria, these bacteria will generally not survive such high temperatures.

In accordance with the present invention, the stripping is carried out in vacuum, viz. under reduced pressure, i.e. at pressures lower than atmospheric, typically lower than 0.5 bara. Preferably the pressure in the stripper is from 0.01 to 0.2 bara, more preferably from 0.05 to 0.1 bara. These low pressures can easily be applied by using vacuum pumps, which are placed down stream of the stripper, in combinations with suitable restriction upstream of the low pressure segment. As a result of these low pressures, the water which contains the sulphides may commence boiling at already very low temperatures, e.g. at about 30° C. It was found that by using very low pressures, $H_2S$ can be removed without heating and bacteria can survive the vacuum stripping step.

By employing a lower pressure, water evaporates from the liquid and the thus formed steam enters the gas phase, where it will (co-)act as a strip gas. Another advantage of the removal of water from the liquid phase is that the concentration of $H_2S$ in the liquid phase increases, as result of which the transfer of $H_2S$ to gaseous phase is further improved. Preferred temperatures for operating the stripper are from 20 to 80° C., more preferably from 25 to 35° C., typically around 30° C.

The mean residence time of the stripping gas in the stripper is typically from 1 to 100 seconds.

One of the advantages of the present invention is that the concentrations of the loaded strip gas, viz. the gas which contains the $H_2S$ stripped from the liquid phase, may be relatively high. Typically, the loaded stripping gas comprises 5-40 wt. % $H_2S$, preferably 25-35 wt. % $H_2S$ on a dry gas basis. High concentrations of $H_2S$ are particularly desirable because the $H_2S$ is to be burnt, as will be explained in more detail hereinbelow. Although the burning of $H_2S$ is exothermic, the amount of heat produced is too low at low $H_2S$ concentrations, thus requiring the addition of extra fuel, which is not desirable from an economic point of view. Thus operating at a $H_2S$ concentration that is as high as possible is desirable. At $H_2S$ concentrations above 4.5 wt. % in air, $H_2S$ can burn in a self supporting flame.

In addition to the steam that is produced in the stripper, extra stripping gas may added to the bottom of the stripper. This extra stream of stripping gas may be e.g. air, which under certain circumstances has additional advantages, as will be explained in more detail hereinbelow. It is also possible to apply this stream of air in a separate stripper, not necessarily a vacuum stripper, which is in line with the vacuum stripper.

In a subsequent step, the loaded stripping gas is subjected to a step wherein the water content of the gas is reduced, e.g. by means of a condenser. In this way a dry $H_2S$ rich stream is produced. Apart from $H_2S$ and depending on the upstream process, the dry $H_2S$ rich gas may comprise other gases, such as $CO_2$. Typically the dry gas further comprises 95-60 wt % $CO_2$, preferably 65-75 wt. % $CO_2$, based on dry gas.

The sulphide containing liquid, from which the sulphide is recovered in accordance with the present invention, may originate from various sources, such as from a wastewater treatment process (such as tannery wastewater); or from a process for the production of fermentation products (such as ethanol, lactic acid, citric acid, etc.).

The (dry) $H_2S$ rich stream produced in accordance with the present invention may be processed further. For instance, it is possible to produce elemental sulphur ($S_x$) from $H_2S$ by means of the well known Claus process.

In a preferred embodiment, however, the $H_2S$ rich gas stream is converted to a stream rich in oxides of sulphur, such as $SO_2$ and/or $SO_3$. Usually this is done by reacting the $H_2S$ with oxygen, whereby the $H_2S$ is thus effectively burnt, whereby normally $SO_2$ is formed. $SO_2$ may consequently be further oxidized to $SO_3$ by means of a suitable catalyst. In a next step the $SO_3$ may be dissolved in water, forming $H_2SO_4$. The burning of the $H_2S$ is preferably carried out using air. As indicated hereinabove, it is even more preferred if the air is entered at the vacuum stripper and/or in the second or further separate stripper, so that it may contribute in stripping action.

In a preferred embodiment of the invention, the liquid feed stream originates from an anaerobic biological wastewater treatment reactor. Such a system effectively converts low value energy of organic compounds that are dissolved in wastewater to high value energy, such as the heat from burnt $H_2S$. This high value energy can be used for different purposes, for example to reduce costs. Thus, this embodiment of the present invention provides in effect a biological heat pump, in which low value energy are converted by using mechanical energy (the compressor) into high value energy.

FIG. 1 shows schematically an embodiment in which two strippers are used in accordance with the present invention. In this embodiment wastewater enters anaerobic reactor 1, in which acidification and sulphate reduction takes place. The liquid effluent is passed to separator 2, from which sludge is returned to reactor 1. The effluent is passed to an anaerobic post treatment process, which is carried out in reactor 3. the liquid effluent of the reactor 3 is passed to stripper 4, which is fed by air at the bottom. The gaseous stream which leaves stripper 4 is rich in air (oxygen) and also contains considerable amounts of $H_2S$ and is subsequently fed to $H_2S$ burner 6, where this gas stream is used as an oxygen source. Another liquid effluent from reactor 1 is fed directly to vacuum stripper 5, which produces a $H_2S$ rich stream that is fed to the burner, where it is burnt using at least part of the oxygen coming from stripper 4. Optionally extra air may be fed to burner 4, if necessary. It is also possible to place stripper 4 before post treatment reactor 3.

In a specific embodiment of the present invention, the stream rich in oxides of sulphur that is produced by oxidizing the sulphides is contacted with water, thus producing a sulphuric acid rich stream, which sulphuric acid rich stream is fed to a step wherein it is contacted with biomass, thus producing a stream rich in monosaccharides and/or polysaccharides, which stream rich in monosaccharides and/or polysaccharides is subsequently subjected to a fermentation step, whereby fermentation products are formed and whereby a sulphate rich stream is formed, which sulphate rich stream is at least in part converted to hydrogen sulphide in said liquid stream, which liquid stream is fed to said stripper.

In wastewater treatment processes, as well as in fermentation production processes, usually one or more alkaline substances are added to the process stream to neutralize acids that are formed at some stage in these processes. The present inventors have found that these alkaline substances, when used, are preferably selected from $Mg(OH)_2$, $NaOH$ and $KOH$. $Ca(OH)_2$ is less preferred, because it may lead to undesired precipitation in the stripping column. $Mg(OH)_2$ is particularly preferred when (baker's) yeast is used, since it is more sensitive to $Na^+$ and $K^+$.

Another application of the present invention is the treatment of tail gas from a Claus plant. In a Claus process oxides of sulphur ($SO_x$) are produced. This $SO_x$ may be absorbed in water and the aqueous stream thus obtained can be treated in the same way as the sulphur compound containing wastewater streams as described herein above. The sulphur compounds are converted to sulphide, which is subsequently stripped in the vacuum stripper in accordance with the present invention. The sulphide can be fed to the burner in the Claus process.

When the process of the present invention is used in producing fermentation products (e.g. ethanol) from lignocellulose, it may be advantageous to take an acidic feed stream that is obtained from the hydrolysis step (by membrane extraction), which is carried out using sulphuric acid and bypass the fermentation reactor. This sulphuric acid stream is then passed directly to the acidification reactor, or even directly to the vacuum stripper because this results in lowering the pH in the stripper, which is favourable for the stripping action, as explained above. The sulphuric acid is maintained in the liquid effluent and fed back to the bioreactor, where it may be converted into sulphide. Thus, according to this preferred embodiment, a relatively clean, acidic wastewater stream is fed to the vacuum stripper, preferably to the top of the vacuum stripper.

The present invention will now be illustrated by the following non-limiting examples.

EXAMPLE 1

To a biological acidification reactor of 5 dm$^3$ was added a synthetic wastewater stream comprising sucrose, yeast extract and sodium sulphate. The amount of sulphur from sulphate was 460 mg S/dm$^3$ and the sucrose amount was 3200 mg/dm$^3$. The pH in the bioreactor was kept constant by feeding NaOH solution using a pH-stat. The effluent of the reactor was allowed to flow to a settling tank (5 dm$^3$) where the sludge was allowed to settle and the liquid was removed. The sludge was returned to the reactor. The liquid effluent was fed to a stripping column (1.5 dm$^3$), which was operated at a pressure of 0.08 bara and a temperature of 30° C. The liquid effluent contained only 10 mg sulphide/dm$^3$. The gas was removed using a membrane pump. No external stripping gas was used.

The sucrose was converted mainly into acetic acid and the sulphate disappeared. The sulphide formed from the sulphate could be removed for 98 wt. % in the vacuum stripper, despite the low H$_2$S concentration in the liquid. The gas from the stripper was subsequently dried by condensing the water. After drying it contained 30 wt. % H$_2$S and 70 wt. % CO$_2$.

It was found that a pH of 6.5 in the bioreactor was optimal. A lower pH resulted in a lower biological activity and a higher pH resulted in a lower stripping efficiency.

After mixing it with air, a gas resulted comprising 9 wt. % H$_2$S and 14 wt. % O$_2$.

EXAMPLE 2

Reference

Example 1 was repeated. Again, the liquid effluent that was fed to the stripper contained 10 mg hydrogen sulphide per dm$^3$ and the pH was 6.5. This time, however, an ordinary (atmospheric) stripper was used, employing N$_2$ as the stripping gas. The dry gas produced contained only 0.25 wt. % H$_2$S.

The invention claimed is:

1. A process for the production of sulphur oxides from a liquid stream comprising hydrogen sulphide, comprising the steps of:
    feeding said liquid stream to a vacuum stripper;
    contacting said liquid stream in said stripper under reduced pressure with a stripping gas, which stripping gas comprises steam that is generated in said stripper, whereby at least part of said hydrogen sulphide is transferred to said stripping gas, whereby a loaded stripping gas is obtained;
    subjecting said loaded stripping gas from said vacuum stripper to a step wherein water is condensed, thus producing a H$_2$S rich stream; and
    burning H$_2$S in said H$_2$S rich stream, thus producing a stream rich in oxides of sulphur wherein said process forms part of a wastewater treatment process; of a process for the production of fermentation products; or of a Claus process.

2. The process according to claim 1, which optionally comprises a further stripper that may be operated under atmospheric conditions.

3. The process according to claim 2, wherein said stripping gas further comprises air and/or CO$_2$ that is fed to said vacuum stripper, to said further stripper if present, or both.

4. The process according to claim 2, wherein air is used for burning H$_2$S, which air is fed as a stripping gas to said vacuum stripper, optionally to said further stripper if present, or both.

5. The process according to claim 1, wherein said loaded stripping gas from said vacuum stripper comprises 5-40 wt. % H$_2$S, based on dry gas.

6. The process according to claim 1, wherein said loaded stripping gas from said vacuum stripper further comprises 95-60 wt % CO$_2$, based on dry gas.

7. The process according to claim 1, wherein water from an anaerobic biological wastewater treatment reactor is treated.

8. The process according to claim 1, wherein water from an anaerobic acidification reactor is treated.

9. The process according to claim 1, wherein said stream rich in oxides of sulphur is contacted with water, thus producing a sulphuric acid rich stream, which sulphuric acid rich stream is fed to a step wherein it is contacted with biomass, thus producing a stream rich in monosaccharides and/or polysaccharides, which stream rich in monosaccharides and/or polysaccharides is subsequently subjected to a fermentation step, whereby fermentation products are formed and whereby a sulphate rich stream is formed, which sulphate rich stream is at least in part converted to hydrogen sulphide in said liquid stream, which liquid stream is fed to said stripper.

10. The process according to claim 1, wherein said stripper is filled with pall rings or saddle rings.

11. The process according to claim 1, wherein the mean residence time of said stripping gas is from 1 to 100 seconds.

12. The process according to claim 1, wherein the pressure in said stripper is from 0.01 to 0.2 bara.

13. The process according to claim 1, wherein an alkaline substance is added in a step prior to the vacuum stripping step.

14. The process according to claim 13, wherein the alkaline substance is Mg(OH)$_2$.

15. The process according to claim 1, wherein a clean, acidic wastewater stream is fed to the vacuum stripper.

16. The process according to claim 15, wherein the clean, acidic wastewater stream is fed to top of the vacuum stripper.

17. The process according to claim 1, wherein the H$_2$S rich stream comprises air.

18. The process according to claim 1, wherein said loaded stripping gas from said vacuum stripper comprises 25-35 wt. % H$_2$S, based on dry gas.

19. The process according to claim 1, wherein said loaded stripping gas from said vacuum stripper further comprises 65-75 wt. % CO$_2$, based on dry gas.

20. The process according to claim 1, wherein the pressure in said stripper is from 0.05 to 0.1 bara.

* * * * *